United States Patent [19]
Manna et al.

[11] Patent Number: 5,527,273
[45] Date of Patent: Jun. 18, 1996

[54] ULTRASONIC LIPECTOMY PROBE AND METHOD FOR MANUFACTURE

[75] Inventors: Ronald R. Manna, Valley Stream, N.Y.; Vaclav Podany, New Fairfield, Conn.

[73] Assignee: Misonix, Inc., Farmingdale, N.Y.

[21] Appl. No.: 319,285

[22] Filed: Oct. 6, 1994

[51] Int. Cl.[6] .................................................. A61B 17/20
[52] U.S. Cl. ............................................. 604/22; 604/902
[58] Field of Search ....................... 604/22, 902; 606/46; 607/97, 115; 128/662.03, 662.06; 601/2

[56] References Cited

U.S. PATENT DOCUMENTS

| | | |
|---|---|---|
| 4,784,971 | 6/1988 | Borodulin et al. . |
| 4,870,953 | 10/1989 | DonMichael et al. . |
| 5,181,907 | 1/1993 | Becker .................................. 604/22 |
| 5,267,954 | 12/1993 | Nita . |
| 5,380,274 | 1/1995 | Nita ...................................... 604/22 |
| 5,397,301 | 3/1995 | Pflueger et al. ..................... 604/22 |
| 5,398,689 | 3/1995 | Connor et al. ................ 128/662.03 |
| 5,419,761 | 5/1995 | Narayanan et al. ................. 604/22 |

*Primary Examiner*—Randall L. Green
*Assistant Examiner*— A. T. Nguyen
*Attorney, Agent, or Firm*—R. Neil Sudol; Henry D. Coleman

[57] ABSTRACT

An ultrasonic lipectomy probe device comprises, in accordance with the present invention, a shank having a proximal end and a distal end, a connector at the proximal end of the shank for connecting the shank to a source of ultrasonic vibrational energy, and an enlarged head at the distal end of the shank. The probe head has a width, in a first direction, substantially larger than an outer diameter of the shank at the distal end thereof. In addition, the head has a thickness, in a second direction essentially orthogonal with respect to the first direction, substantially equal to the outer diameter of the shank. Accordingly, the probe head is flattened, for facilitating the removal of fat in accordance with the present invention. In most applications, the shank is provided with a longitudinally extending channel, while the head may be provided with a pair of inlet bores communicating with the channel and extending at substantial angles to the channel on substantially opposite sides thereof.

27 Claims, 3 Drawing Sheets

ULTRASONIC LIPECTOMY PROBE AND METHOD FOR MANUFACTURE

BACKGROUND OF THE INVENTION

This invention relates to an ultrasonic lipectomy probe and a method for manufacturing the probe. In addition, this invention relates to a lipectomy procedure or methodology which utilizes the probe.

Over the last 15 to 20 years, a procedure has been developed to remove unwanted fatty deposits from the human body in a hospital or clinical setting.

This procedure involves creating an incision in the skin, inserting an essentially hollow probe into the area between the dermis and underlying muscle. By connecting the other end of the probe to a vacuum source, the fat is effectively sucked from the area due to the differential pressure which exists across the probe's inlet orifice. By manipulating the probe in and out of the area, a large amount of fatty deposit may be removed and the existing bulges flattened, thereby improving the appearance of the person. Areas of the body which respond well to this procedure are the outer thighs ("saddlebags"), inner thighs, lower abdominal area, hip ("love handle") area and around the jowl areas of the face. The procedure has been dubbed "suction assisted lipectomy" or "liposuction" and it is currently a major source of revenue for the cosmetic surgery industry.

Although the esthetic benefits of this procedure are well documented, it is not without risk to the patient. Blood loss is a concern in some cases because the tissue is being ripped from the body and there is no differentiation between fat ripped from the body and there is no differentiation between fat and connective tissue or blood vessels. The physician must also use a great deal of force to push the probe in and out of the body, thereby inducing trauma to the surgical site or fatty deposit area. It is not uncommon for the patients to become severely bruised and tender in these areas for several days or even weeks after the procedure. Also, blood loss has been a problem in certain procedures, as the blood vessels are damaged by the thrusting of the probes and the trauma induced by the suctioning.

Another limitation using simple suction to remove the fat is that sculpturing of the area is not easily accomplished. Since the only tissue which is removed is that which is situated directly opposed to the inlet orifice, the probe creates channels or tunnels in the fat. By moving the probe in and out, a checkerboard or waffle pattern is created. The peaks of fat which are not removed then fold over and the area can be rendered fairly smooth as opposed to lumpy. However, the fringes of the deposit area cannot be feathered in to create a smooth transition between the liposuctioned area and the natural tissue immediately surrounding it. In some cases, a crater can be formed in the area where the fat was removed. This can be as unsightly as the original lump and is even more difficult to treat. Recently, several inventors have sought to activate the liposuction probes with high powered ultrasonic vibrations. See, for example, U.S. patent application Ser. No. 08/101,188, now U.S. Pat. No. 5,419,761.

In ultrasonic lipectomy procedures, the suction probe is connected to an electromechanical transducer of either magnetostrictive or electrostrictive design. Once the transducer is activated, longitudinal vibrations are set up in the probe and the distal end is turned into a vibrating wand which serves to liquefy the fat which comes into contact with it. The resultant fatty emulsion is then removed from the body much in the same way as the standard liposuction techniques, by way of a suction source and collection bottle. Several advantages are gained by the use of this equipment. First, the level of vacuum needed to remove the fat is substantially less than that needed for the standard liposuction procedure. Also, the probe will liquefy all of the tissue surrounding the distal end, which makes the probe easier to insert and retract from the body. This reduces the trauma to the patient, not to mention the reduction of effort needed by the surgeon. The benefit here is less fatigue on the part of the physician, thereby allowing him to be more alert and able to perform more procedures per day. In addition, less bleeding has been noted during trials of these devices, since ultrasound has been shown to have a cauterizing effect on small blood vessels. U.S. patent application Ser. No. 08/101,188, now U.S. Pat. No. 5,419,761 to Alliger et al. outlines several of these advantages.

Liposuction probes developed to date, whether for conventional vacuum assisted procedures or newer ultrasonically assisted ones, have basically been formed of tubular stainless steels or titanium. The distal ends of the probes have been closed or blunted to eliminate sharp corners which could cause injury when inserted into the body. In some cases, the inlet orifices have been disposed along a sidewall of the probe, so that the probe must be twisted during insertion to remove tissue evenly from the body cavity. The purpose of situating the orifice in this manner is to allow discrimination as to where the tissue is removed. For instance, if the orifice was pointed away from the underside of the dermis, the dermis would not be harmed by tissue fragmentation and removal.

While the tubular cannula designs discussed above are effective for use in conventional vacuum assisted liposuction procedures, they are not readily adaptable to the newer field of ultrasonically assisted liposuction. Here, other factors come into consideration when the design of the liposuction probe is undertaken. Since the probe is now being vibrated at ultrasonic frequencies (typically 16 to 60 kc), it is subjected to stresses and fatigue not encountered in the passive probes of current liposuction tooling. In addition, the ultrasonic probe must be designed to provide sufficient multiplication of the amplitude input provided by the transducer which drives it. Since straight cylindrical probes do not provide gain for ultrasonic vibrations, the probes must be driven at the high input amplitudes necessary for tissue liquefication. This, in turn, causes high stress concentrations at the node points, or points where the vibratory motion in the standing wave is zero. When stresses in vibratory elements are high, a material heating problem occurs. The temperature of the probe at the stressed node points elevates and the potential for tissue burning or charring exists. In a liposuction application, this phenomenon must be avoided, since the probes are inserted deeply into the body and burning could cause damage to the lower levels of the dermis, leading to scarring, infection, etc.

Accordingly, straight probes have not been proven particularly suitable for use in ultrasonic procedures even if the probes are adapted and tuned to resonate at the driving frequencies of the transducer system. U.S. Pat. No. 4,886, 491 to Parisi et al., U.S. Pat. No. 5,123,903 to Quaid, and U.S. Pat. No. 5,419,761 to Alliger et al. all show typical embodiments for ultrasonic probes used in liposuction procedures. In practice, these probes have heated significantly at the nodal regions, been prone to fracture at higher vibratory amplitudes and have a tendency to break into transverse motion, wherein the tips of the probes whip, causing fracturing and the possibility of leaving pieces of metal in the operating field. Damage to the tissue not normally associated with a properly designed ultrasonic element may also occur. This fact is indirectly acknowledged in U.S. Pat. No. 4,886,491 which prescribes low amplitude vibrations of 2 mils peak-to-peak (50 microns pp). However, amplitudes in this range have been shown not to be adequate for liquefying certain fatty deposits of the body, especially those in the saddlebag areas.

OBJECTS OF THE INVENTION

An object of the present invention is to improve the performance of probes used for ultrasonically assisted liposuction procedures.

Another object of the present invention is to provide an ultrasonic lipectomy probe which has a reduced chance of fatigue failure.

Another, related, object of the present invention is to provide an ultrasonic lipectomy probe which remains cool during prolonged operation, thereby eliminating the danger of tissue damage due to high temperature levels.

A further object of the present invention is to provide such an ultrasonic lipectomy probe which exhibits high distal amplitude levels.

Yet another object of the present invention is to provide an ultrasonic lipectomy probe which has an enhanced ability to remove adipose tissue during a lipectomy procedure.

An additional object of the present invention is to provide an improved method for manufacturing an ultrasonic lipectomy probe.

Yet another object of the present invention is to provide an improved lipectomy procedure.

These and other objects of the present invention will be apparent from the drawings and detailed descriptions herein.

SUMMARY OF THE INVENTION

An ultrasonic lipectomy probe device comprises, in accordance with the present invention, a shank having a proximal end and a distal end, a connector at the proximal end of the shank for connecting the shank to a source of ultrasonic vibrational energy, and an enlarged head at the distal end of the shank.

In most applications, the shank is provided with a longitudinally extending channel, while the head is provided with a pair of inlet bores communicating with the channel and extending at substantial angles to the channel on substantially opposite sides thereof. The channel or lumen is a passageway for applying suction during a lipectomy procedure to remove adipose tissues which have been liquefied by ultrasonic cavitation.

According to an important feature of the present invention, the head of the lipectomy probe has a width, in a first direction, substantially larger than an outer diameter of the shank at the distal end thereof. In addition, the head has a thickness, in a second direction essentially orthogonal with respect to the first direction, substantially equal to the outer diameter of the shank. Accordingly, the probe head is flattened, for facilitating the removal of fat in accordance with the present invention. Preferably, the first direction and the second direction are both substantially orthogonal to the channel of the instrument.

According to another feature of the present invention, the shank includes at least one section of reduced diameter at the distal end for amplifying an amplitude of vibration at the head relative to a magnitude of vibration at the proximal end of the shank. The reduction in diameter is implemented, for example, by an exponential taper in a manner similar to a conventional ultrasonic transducer horn.

According to a further feature of the present invention, the suction channel has a distal diameter which is smaller than a proximal diameter of the suction channel. In other words, the suction channel increases in diameter from the distal end towards the proximal end, for purposes of reducing clogging and facilitating fat removal.

According to an additional feature of the present invention, the probe head includes a plug element inserted into a recess in the distal end of the shank, the inlet or suction bores being provided in the plug element. The bores may be machined into the plug element either before or after the plug element is attached to the probe shank.

According to yet another feature of the present invention, the shank includes a plurality of distinct shank pieces or sections joined to one another at an antinode. This facilitates manufacture of the ultrasonic lipectomy probe and further facilitates repair or replacement of the distal end of the probe.

In a particular embodiment of an ultrasonic lipectomy probe in accordance with the present invention, the shank includes a proximal section of a first external diameter, a central section of a second external diameter and a distal section of a third external diameter. The first external diameter is greater than the second external diameter, while the second external diameter is greater than the third external diameter. This reduction in diameter serves to enhance the power output of the device.

According to yet a further feature of the present invention, the probe head has an external dimension more than three times as large as a maximum external dimension of the shank at the distal end thereof.

A method for manufacturing an ultrasonic lipectomy probe comprises, in accordance with the present invention, the steps of providing an elongate shank section, forming a longitudinally extending channel in the shank section, providing a plug element with at least one inlet bore, and inserting the plug element into the channel at a distal end of the shank section so that the bore communicates with the channel.

Pursuant to another feature of the present invention, this method further comprises the step of bonding the plug element to the shank section upon insertion of the plug element into the channel. The bonding may include beam welding the plug element to the shank section, brazing the plug element to the shank section, and/or gluing the plug element to the shank section.

In addition, or alternatively, the plug element may be provided with an external screw thread, in which case the method further comprises the step of forming an internal screw thread at the distal end of the channel, while inserting the plug element into the channel includes the step of screwing the plug element into the channel.

A method for manufacturing an ultrasonic lipectomy probe comprises the steps of (i) providing an elongate first shank section and an elongate second shank section, (ii) providing the first shank section with means at one end of the first shank section for connecting the first shank section to a source of ultrasonic vibrational energy, (iii) forming longitudinally extending channels in the first shank section and the second shank section, (iv) upon formation of the channels, connecting another end of the first shank section to a first end of the second shank section at a junction point so that the channels in the first and the second shank section communicate with one another in a completed ultrasonic probe shank. In accordance with this method, the first shank section and the second shank section have predetermined lengths so that the junction point is located at an antinode of the completed probe shank.

In accordance with another feature of the present invention, the connecting of the two shank sections is implemented by bonding another end of the first shank section to the first end of the second shank section. The bonding step may include the step of beam welding the first shank section to the second shank section, brazing the first shank section to the second shank section, and/or gluing the first shank section to the second shank section. Alternatively, or additionally, the shank sections may be provided with screw threads and screwed to one another.

An ultrasonic lipectomy method in accordance with the present invention utilizes an ultrasonic lipectomy probe device comprising a shank having a proximal end and a distal end, means at the proximal end of the shank for connecting the shank to a source of ultrasonic vibrational energy, and a substantially enlarged head at the distal end of the shank. The method includes the steps of (a) forming an incision in a skin surface of a patient, (b) inserting the head and a distal end segment of the shank through the incision and into subcutaneous adipose tissues of the patient, (c) upon insertion of the head through the incision, generating an ultrasonic pressure wave at the proximal end of the shank, (d) transmitting the ultrasonic wave through the shank to establish a longitudinal standing wave therein, (e) producing cavitation bubbles at the head in response to the standing wave, (f) by virtue of the production of the cavitation bubbles, liquefying adipose tissues of the patient at a surgical site located distally of the head, and (g) manipulating the probe device from outside the patient during the steps of generating, transmitting, producing and liquefying, so that the probe head moves from side to side.

Where the shank has a channel extending longitudinally from the proximal end to the distal end, this method further comprises the step of applying suction to the channel during the manipulation of the probe, thereby aspirating the liquefied adipose tissues from the surgical site through the channel.

Where the head is provided with a pair of inlet bores communicating with the channel and extending at substantial angles to the channel, this method further includes the step of aspirating the liquefied adipose tissues from the surgical site through the inlet bores and into the channel.

An ultrasonic lipectomy probe in accordance with the present invention is generally, but not exclusively, hollow in cross section. The proximal end of the device terminates in a hollow threaded stud which allows attachment to an ultrasonic transducer of either electrostrictive or magnetostrictive design. The external shape of the probe permits amplification of the input amplitude to a sufficient output amplitude at the distal end to effectively liquefy fatty or tumor tissue by cavitational energy. This overall shaping may be described as follows. The first half-wavelength of the device is configured to provide a gain substantially lower than the overall gain needed to obtain the final amplitude. The smaller diameter of the next section is extended as far as necessary to obtain the proper working length for the probe. The final half wave section is shaped to provide the additional gain necessary for the device. The tip or head portion is enlarged in various shapes to provide a greater active surface area. The high output amplitude and the greater surface area provided by the enlarged tip portion result in more tissue ablation in a given period of time than is accomplishable by a thinner wall section, thereby reducing the time of an operative lipectomy procedure.

The distal orifices or inlet bores in accordance with the present invention provide a straighter path for the liquefied tissue, thereby reducing the tendency for clogging and easing cleaning of the probe after each procedure. Where the distal end of an ultrasonic lipectomy is formed from a plug, manufacturing is simplified and facilitated. In addition, scrap is reduced and the cost of production is lowered.

Although a probe in accordance with the present invention may be of a one piece design, it may also be designed in a multi-piece configuration which facilitates manufacture, lessens replacement cost and allows more precise tuning after assembly. Although titanium alloy has been shown to be an excellent material choice, other metals may be employed in some designs with equal results. In fact, a probe made of several dissimilar metals, such as aluminum and titanium may be manufactured without circumventing the intent of this disclosure.

Ultrasonic lipectomy probes in accordance with the present invention experience relatively low internal stresses, which allows the probes to remain cool during prolonged operation, while providing high distal amplitude levels. These high amplitude levels increase the effectiveness of the probes in disintegrating fat by cavitational energy. Lower stress levels also extend the useful life of the probes by reducing fatigue failures. The stepped or reduced-diameter shank designs in accordance with the present invention reduce the tendency for the probes to break into transverse vibration. The enlarged tip designs aid in the removal of fat from the operative site and decrease the time typically needed for ultrasonic liposuction procedures. All of these features permit the use of thinner tools so that sculpturing is also possible. The devices outlined in this disclosure have been proven effective for use in liposuction procedures both in bench top studies and in actual clinical cases.

DETAILED DESCRIPTION

A correctly designed ultrasonic liposuction probe must take several application requirements into consideration. First, the vibratory frequency must be specified. Then, the length of probe which must be inserted into the body cavity must be ascertained. In cases where the saddlebag area is to be sculpted, for instance, the length of active probe necessary has been shown to be a minimum of 25 cm. Next, the diameter of the cannula must be determined. For the saddlebag area, again, a 4 mm to 7 mm probe is useful. This specification sets the maximum diameter of the probe section to be inserted into the patient, but smaller cross sections are permitted at different lengths along the probe itself.

The tip design is another factor which should be addressed before a detailed design of the probe is undertaken. Different tip configurations are provided, as discussed below, for ultrasonic liposuction in different areas of the body. For instance, in bulk removal, the tip may have a blunted tip with a concentric inlet orifice, rendering the probe hollow from the proximal to the distal end. In cases where removal of facial deposits are required, a bullet shaped tip with side orifices can be used, so that the distal end of the probe may be placed closer to delicate nerve bundles without the risk of suction damage.

Finally, the maximum distal end vibratory amplitude should be specified. The maximum amplitude of vibration depends upon the tissue characteristics in the area of the body to be treated, as well as the frequency of operation and the maximum diameter of the cannula. It has been found in clinical work that the amplitude necessary for disruption and liquefication of the stomach and facial deposits is lower then that needed for the tougher areas of the thighs. The stomach and facial areas have been disrupted with as little as 90 microns peak-to-peak ("p-p") of vibratory displacement, while the saddlebag areas of physically fit patients need closer to 140 microns p-p. Accordingly, if the transducer's maximum output amplitude is fixed, as generally is the case, then the probe's gain factor will have to be adjusted to achieve the desired level of displacement.

Pursuant to the above-related considerations, a preferred embodiment of a 22 kc, 7 mm probe for removing fat in the outer thigh (saddlebag) area could be described as follows.

Since the half wavelength dimension for 6AL4V titanium alloy (a common probe material) vibrating at 22 kc is approximately 13 cm, a multi-wavelength design is generally needed to provide an active insertable probe length of 25 cm. As is generally accepted in the design of ultrasonic tooling, the probe design must comprise integer multiples of one-half wavelengths of the operating frequency. The first half wavelength of the probe is designed such that the amplitude gain factor is somewhat less than that needed for the overall probe.

Figure 1:
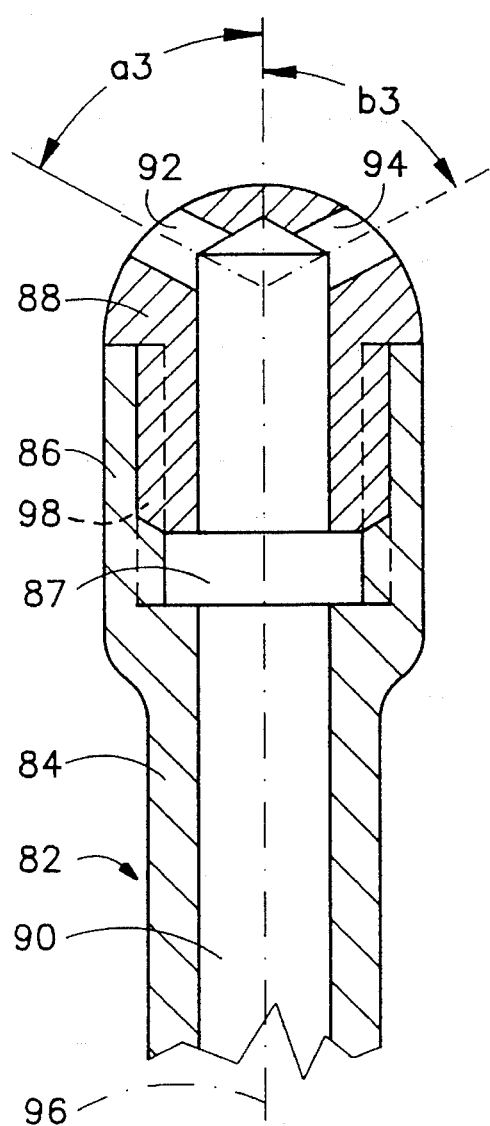
FIG. 1 is a side elevational view, partly in cross-section, of an ultrasonic lipectomy probe in accordance with the present invention.

As shown in FIG. 1, an ultrasonic lipectomy probe in accordance with the above-discussed considerations comprises an elongate shank or shaft 10 having a threaded connector or stud 12 at a proximal end and a cavitation head or tip 14 at a distal end. Connector 12 serves to connect shank 10 to a conventional electrostrictive or magnetostrictive source (not shown) of ultrasonic vibrational energy. Shank 10 includes a generally cylindrical proximal section 16 of a first external diameter, a generally cylindrical central section 18 of a second external diameter and a generally cylindrical or slightly tapered distal section 20 of a third external diameter. The diameter of proximal shank section 16 is greater than the diameter of central shank section 18, which is in turn greater than the diameter of distal shank section 20. Shank sections 16 and 18 are joined to one another at 22 in a step radius, or an exponential (shown), Fourier or catenoidal curve. Similarly, shank sections 18 and 20 are joined to one another at 24 in a step radius, or an exponential (shown), Fourier or catenoidal curve. Where the probe of FIG. 1 is used in fat reduction in the outer thigh area, the diameter of central shank section 18 is in a range of 7 mm.

Shank 10 is provided with a longitudinally or axially extending channel, lumen or bore 26 which is connected at a proximal end, via an ultrasonic transducer assembly (not shown), to a vacuum generator or suction source (not shown) for purposes of removing liquefied adipose tissue from a surgical site during a lipectomy procedure. The ultrasonic transducer assembly may take the form of the assembly described and illustrated in U.S. patent application Ser. No. 08/127,641, filed Sep. 28, 1993, now U.S. Pat. No. 5,460,054, the disclosure of which is hereby incorporated by reference. Preferably, channel 26 has a larger diameter at the proximal end of shank 10 than at the distal end thereof, whereby fat removal is facilitated.

The diameter of proximal or input shank section 16 is chosen to provide a gain which is lower than the overall gain needed for the probe assembly, but is high enough to allow the stresses in the shank section to be approximately 20,000 psi. It is to be noted that, although this value is significantly lower than the ultimate or yield stresses generally quoted for 6AL4V titanium alloy, it has been found that this stress level takes into account internal loss factors which would otherwise heat or destroy the probe if it were operated close to yield. Other materials would require the stress level to be reevaluated. Of course, the diameter of central bore or channel 26 must be taken into consideration as well. Bore or channel 26 should be as large as practical, in order to prevent clogging of the probe with congealed fat, while keeping the stress levels below the prescribed limit.

Central shank section 18 has a uniform diameter and extends for at least three-quarters wavelength, while distal shank section 20 extends for a quarter wavelength. Distal shank section 20 is shaped to provide the gain necessary to achieve the necessary overall tip amplitude. By the reduced outside diameter of the distal shank section, the gain of the probe will be increased and power output of the device is enhanced.

Depending upon the overall gain needed, the total length of the reduced diameter shank sections 18 and 20 is variable.

At a point approximately ⅛ to 1/16 of the operating wavelength from a distal end of the probe, the diameter of the probe is increased to that of the maximum permissible diameter, in this case 7 mm, to form cavitation head 14. The diameter of head 14 may be greater than the shank diameter, as discussed in detail hereinafter with reference to FIGS. 2A, 2B, 3A, 3B, 4A, 4B, and 5A, 5B. Enlarging the cavitation head increases the active distal area and concomitantly increases the rate of tissue liquefication. It should be noted that abrupt changes in diameter are not desired, since stress risers can occur, which, if the maximum stress exceeds the material limits, will cause fracturing. It is more desirable that smooth transitions, such as a cove radius or exponential curve be used instead.

The probe of FIG. 1 is finished by designing the proper shape of head or tip 14, whether it is blunted or bullet shaped. The lengths of all shank sections 16, 18, and 20, including head 14, may be calculated using engineering techniques well known in the art of ultrasonic probe engineering. Such design formulas can be found in the texts "Ultrasonics" by Benson Carlin (1960 McGraw-Hill) or "Sonics" by Hueter and Bolt (1955 J. Wiley and Sons).

Generally, connector or stud 12 is machined as an integral part of shank 10 and particularly proximal shank section 16. However, a separate stud (not shown) may be used if the proper liquid sealing provisions are made. Of course, threaded connector or stud 12 is hollow owing to an extension of channel or bore 26 through the stud.

FIGS. 2A, 2B, 3A, 3B, 4A, 4B, and 5A, 5B illustrate several tip configurations of an ultrasonic lipectomy probe. All of these configurations can have a stepped or multidiameter shank, as described hereinabove with reference to FIG. 1. The basic principle behind the designs of FIGS. 2A, 2B, 3A, 3B, 4A, 4B, and 5A, 5B is the increase in tip surface area in one plane, while the thickness of the probe in the direction normal to said plane is held to the maximum specified at the time of design. In other words, the lipectomy probe heads each have a width, in a first direction, substantially larger than an outer diameter of the shank at the distal end thereof.

Figure 2A:
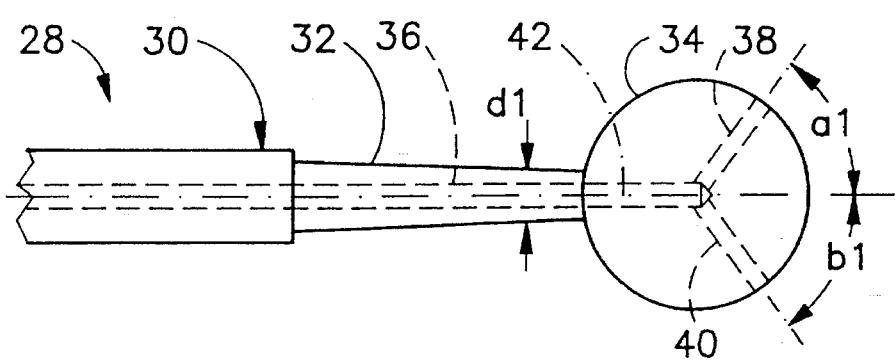
FIG. 2A is a partial side elevational view of an ultrasonic lipectomy probe with an enlarged head in accordance with the present invention.
Figure 2B:
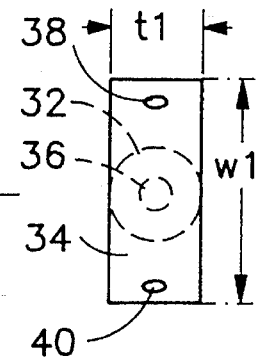
FIG. 2B is a partial front elevational view of the probe of FIG. 2A.

For instance, FIG. 2A shows a lipectomy probe 28 having an elongate shank or shaft 30 with a distal shank section 32 having a circular cross section in the plan view (FIG. 2B). Probe 28 has an enlarged head or tip portion 34 which is flattened. More particularly described, head 34 of probe 28 has a width w1, in a first direction, which is substantially larger than an outer diameter d1 of distal shank section 32, particularly at the distal end thereof. In addition., head 34 has a thickness t1, measured in a second direction essentially orthogonal with respect to the direction of measurement of width w1, substantially equal to outer diameter d1 of shank section 32. Width w1 and thickness t1 are measured substantially orthogonally with respect to a longitudinally or axially extending channel or lumem 36 of probe 28. The flattening of probe head 34 serves to facilitate the removal of fat in certain applications.

As further illustrated in FIGS. 2A and 2B, head 34 is provided with a pair of inlet bores 38 and 40 communicating with channel 36 and extending at substantial angles a1 and b1 with respect to the channel on substantially opposite sides thereof. Angles a1 and b1 are approximately 60° in the embodiment of FIGS. 2A and 2B. However, virtually any angle with respect to channel 36 or an axis 42 thereof may be utilized.

Figure 3A:
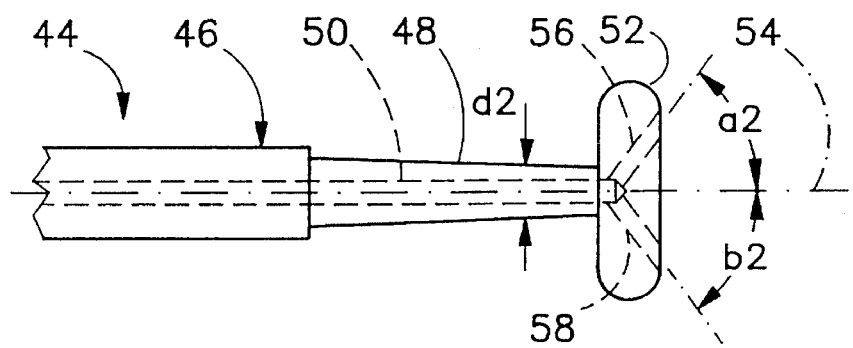
FIG. 3A is a partial side elevational view of another ultrasonic lipectomy probe with an enlarged head in accordance with the present invention.
Figure 3B:
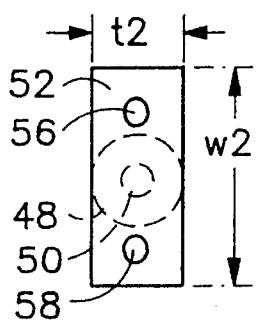
FIG. 3B is a partial front elevational view of the probe of FIG. 3A.

FIGS. 3A and 3B show another lipectomy probe 44 having an elongate shank or shaft 46 with a substantially cylindrical or slightly tapered distal end section 48. Probe 44 has a longitudinal or axial suction channel or lumen 50 and a head or tip portion 52 which is flattened in a first direction perpendicular to an axis 54 of the probe and enlarged in a second, mutually orthogonal direction also perpendicular to axis 54. More specifically described, head 52 of probe 44 has a width w2, in the first direction, which is substantially larger than an outer diameter d2 of distal shank section 48, particularly at the distal end thereof. In addition, head 52 has a thickness t2, measured in the second direction, which is substantially equal to outer diameter d2 of shank section 48.

As further illustrated in FIGS. 3A and 3B, head 52 is provided with a pair of inlet bores 56 and 58 communicating with channel 50 and extending at substantial angles a2 and b2 with respect to the channel on substantially opposite sides thereof. Angles a2 and b2 are approximately 60° in the embodiment of FIGS. 3A and 3B. However, virtually any angle with respect to channel 50 or an axis 54 thereof may be utilized.

Figure 4A:
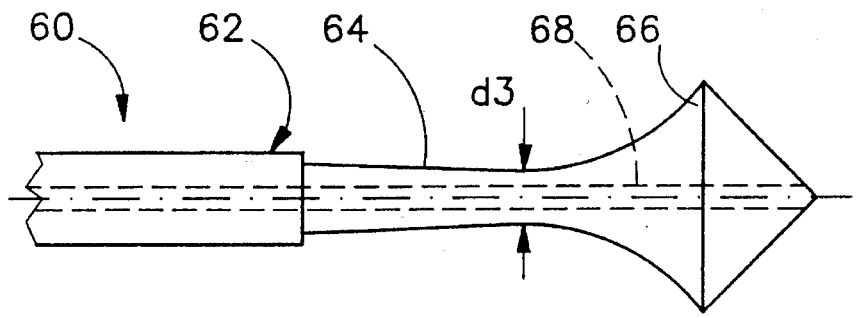
FIG. 4A is a partial side elevational view of a further ultrasonic lipectomy probe with an enlarged head in accordance with the present invention.
Figure 4B:
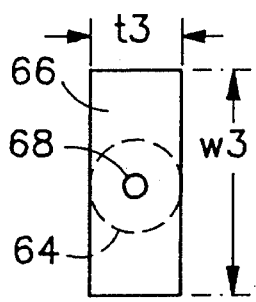
FIG. 4B is a partial front elevational view of the probe of FIG. 4A.

FIGS. 4A and 4B depict a further lipectomy probe 60 having an elongate shank or shaft 62 with a distal end section 64 and a head or tip portion 66 which is enlarged in a first direction and flattened in a second direction. A longitudinal or axial suction channel 68 extends the length of shank 62 and through head 66.

Head 66 of probe 60 has a width w3, in the first direction, which is substantially larger than an outer diameter d3 of distal shank section 64, particularly at the distal end thereof. In addition, head 66 has a thickness t3, measured in the second direction essentially orthogonal with respect to the direction of measurement of width w3, which is substantially equal to outer diameter d3 of shank section 64. Width w3 and thickness t3 are measured substantially orthogonally with respect to channel or lumen 68 of probe 60.

Figure 5A:
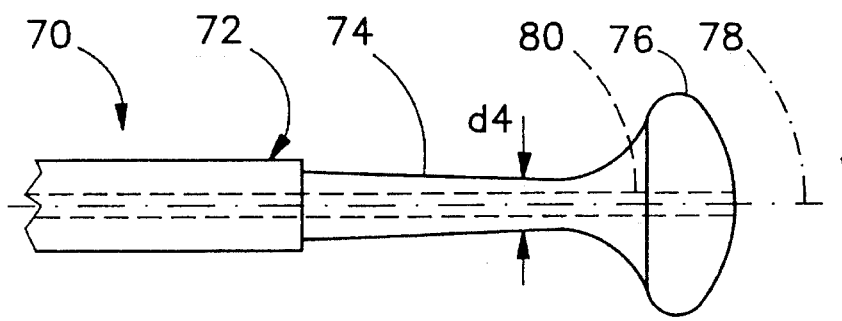
FIG. 5A is a partial side elevational view of an additional ultrasonic lipectomy probe with an enlarged head in accordance with the present invention.
Figure 5B:
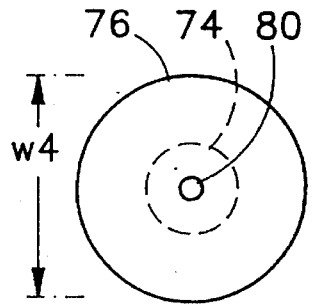
FIG. 5B is a partial front elevational view of the probe of FIG. 5A.
Figure 7:
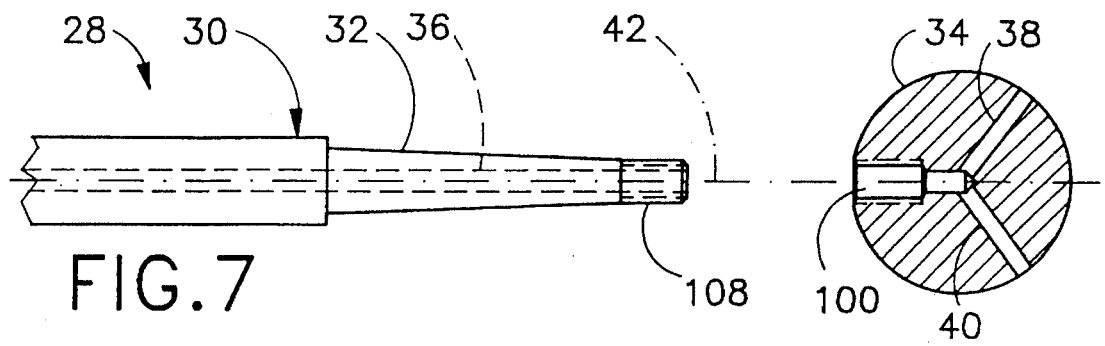
FIG. 7 is an exploded partial longitudinal cross-sectional view depicting a method of manufacturing the ultrasonic lipectomy probe of FIGS. 2A and 2B.
Figure 8:
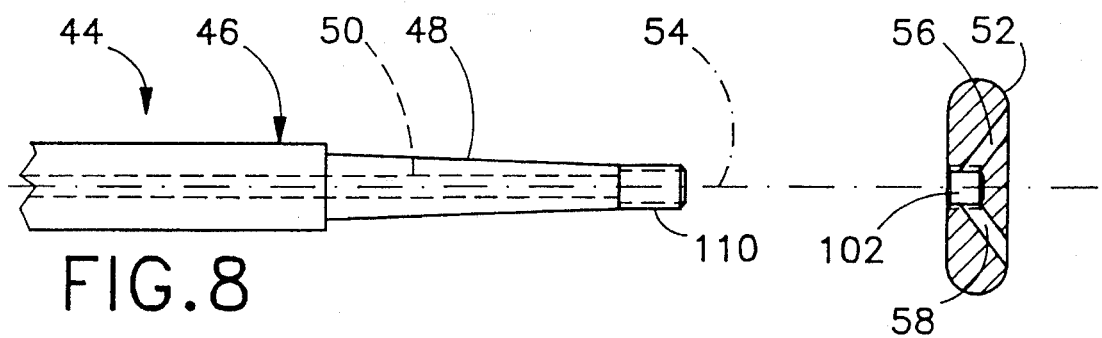
FIG. 8 is an exploded partial longitudinal cross-sectional view showing a technique for manufacturing the ultrasonic lipectomy probe of FIGS. 3A and 3B.
Figure 9:
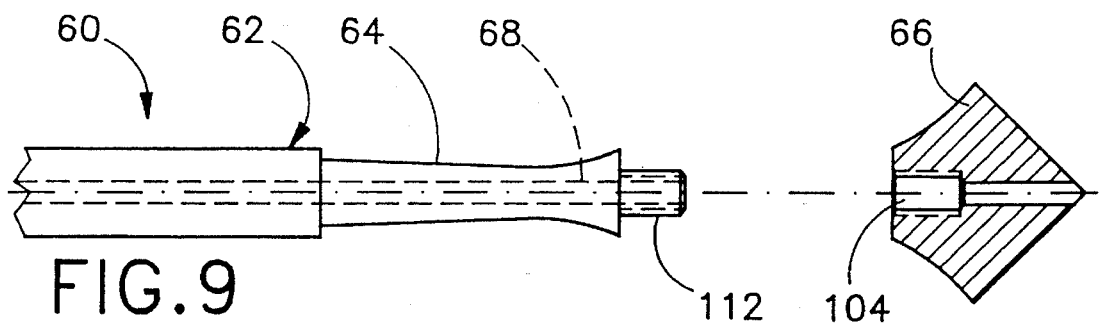
FIG. 9 is an exploded partial longitudinal cross-sectional view illustrating a process step in manufacturing the ultrasonic lipectomy probe of FIGS. 4A and 4B.
Figure 10:
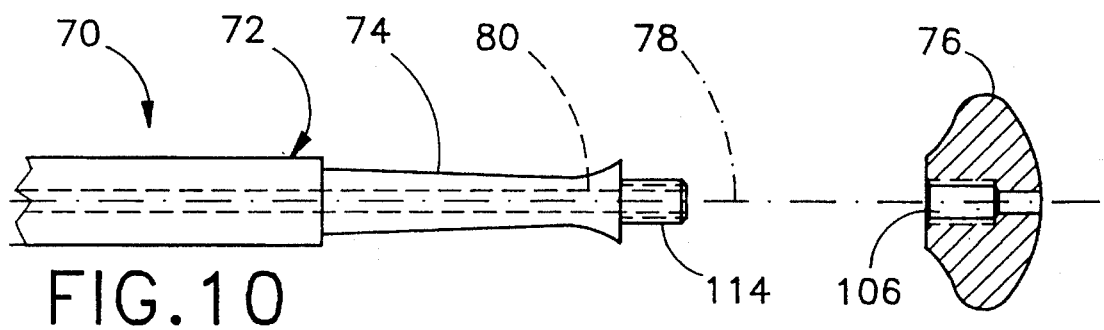
FIG. 10 is an exploded partial longitudinal cross-sectional view depicting a step in making the ultrasonic lipectomy probe of FIGS. 5A and 5B.

As depicted in FIGS. 5A and 5B, another lipectomy probe 70 has an elongate shank or shaft 72 with a distal end section 74 and a head or tip portion 76 which is enlarged symmetrically about an axis 78 of the probe. Probe shank 72 is provided with a suction channel or lumen 80 which extends through head 76.

In using the probes 28, 44, 60, and 70, a surgeon creates an incision in a skin surface of a patient, the incision having the width w1, w2, w3, w4 of the respective probe head 52, 66, 76. Probe head 34, 52, 66, 76 is inserted through the incision and, subsequently, the surgeon manipulates the probe so as to swing the probe head from side to side. During this swinging sideways motion, an ultrasonic pressure wave generated at the proximal end of shank 30, 46, 62, 72 is transmitted through or along the shank to establish a longitudinal standing wave therein. Cavitation bubbles produced at the head 34, 52, 66, 76 in response to the vibration thereof by the standing wave liquefy adipose tissues of the patient at a surgical site located distally of the head. The liquefied adipose tissue is suctioned from the surgical site through channel 36, 50, 68, 80.

This ultrasonically assisted liposuction technique, as well as the enlarged head of the ultrasonic lipectomy probe, produces, a flatter and more esthetically pleasing result than obtainable using a purely cylindrical horn, which creates a waffled pattern when used pursuant to current procedures.

Multiple inlet bores or orifices 38, 40 and 56, 58, as shown in FIGS. 2A, 2B and 3A, 3B, serve to increase the amount of liquefied tissue removed over time. The overall diameter of cavitation head 34, 52, 66, 76 is somewhat arbitrary. That diameter maybe three times the outer diameter d1, d2, d3, d4 of the respective distal shank section 32, 48, 64, 74 or greater. However, care should be taken not to increase the diameter to the point where it is greater than the quarter wavelength of the operating frequency, since radial or diaphramic vibration resonances may be induced, which may cause undue heating or failure.

Figure 6:
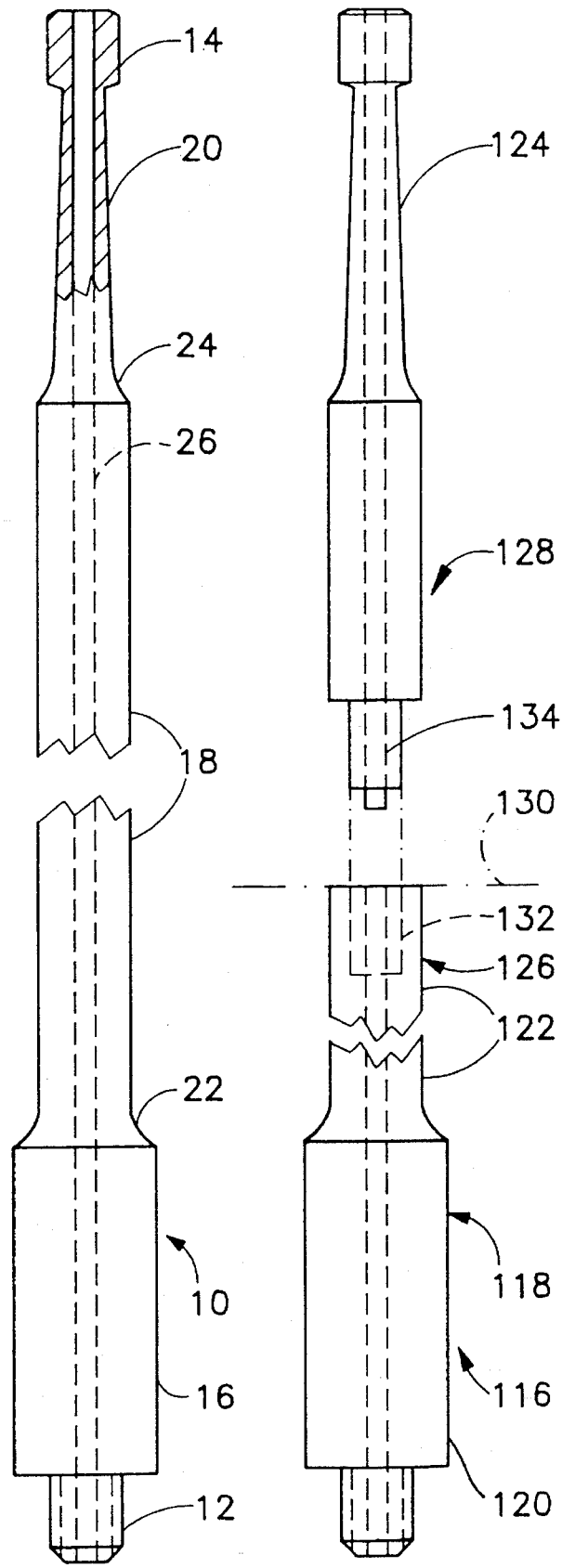
FIG. 6 is a partial longitudinal cross-sectional view, on a substantially enlarged scale, of an ultrasonic lipectomy probe with a plug element probe head in accordance with the present invention.

FIG. 6 shows an improvement in head design in a case where increased head diameter is not desired. As shown in FIG. 6, an ultrasonic lipectomy probe 82 is provided, at a distal end of a distal shank section 84, with a head or tip portion 86 having a recess 87 which receives a plug element 88. Head 86 with plug-element 88 is shaped like a bullet. A central suction channel or lumen 90 of probe 82 is split into two channels or inlet bores 92 and 94 in plug element 88 by drilling the bores at angles a3 and b3 of approximately 60 degrees from a longitudinal axis 96. It is to be noted that 60 degrees is not critical for angles a3 and b3. Therefore, any angle would fall within the scope of this invention. As in other embodiments detailed herein, the provision of multiple inlet bores 92 and 94 achieves a greater active area without resorting to a larger cross sectional diameter.

Inlet bores 92 and 94 are of smaller diameter than channel 90. By so making inlet bores 92 and 94 of smaller diameter, the same amount of liquefied tissue may be removed by suction as with a single large bore channel. However, the manufacture of the probe of FIG. 6 requires a novel design and assembly method which can be described as follows.

Deep gun drilling of metals is a fairly expensive, delicate process, especially in metals such as titanium or stainless steels. In order to make these probes in one piece, which is preferred due to the inherent problems with joining ultrasonic tooling along a small diameter shank, the length of the hole needed exceeds 30 cm. If one attempts to drill the main suction channel from one end of the probe only, the small diameter drill frequently "walks" or drifts, thereby rendering the bore asymmetrical. In extreme cases, the drill may even break through the sidewall of the billet, thereby rendering the piece scrap. Therefore, most gun drilling vendors prefer to drill the holes from both ends, i.e., drill halfway through and reverse the piece in the mandrel and complete the bore from the other side. A slight jog or mismatch may occur at the meeting of the two bores, but this result is not consequential in most cases.

As can be inferred from the foregoing description of the gun drilling process, the horn tip design must accommodate the bore hole at the tip or be drilled "blind." In manufacturing the ultrasonic lipectomy probe 82 of FIG. 6, the probe may be gun drilled from both sides. Then head or tip 86 is machined to generate recess 87 for accepting plug element 88. Plug element 88 must have a length sufficient to bring the resonant frequency of the completed probe 82 into specification. Bores or orifices 92 and 94 may be drilled before or after assembly of plug element 88 to distal shank section 84, although drilling bores 92 and 94 before the assembly process will ease deburring and cleaning of those smaller orifices. It has been shown that a machine thread 98 is sufficient to maintain plug element 88 coupled to head 86 during normal usage and sterilization. However, for increased safety, plug element 88 may be electron beam welded, brazed or glued in place with epoxy compounds. Final tuning may be obtained by machining the final shape of the tip after assembly and welding, if needed.

In cases where the probe diameter is too small to allow machine threads to be formed, a press fit plug section may be utilized. Here the tip of the probe is gun drilled in the manner previously described. The distal end is then machined to accept the press plug. After insertion of the plug, the distal end is finished machined for shape and frequency. Again, for more security, the plug may be beam welded, brazed or glued in place. Probes utilizing both these techniques have successfully been used and sterilized in dozens of procedures without failure.

The above-described design and manufacturing techniques may be used for the different tip profiles of FIGS. 2A, 2B, 3A, 3B, 4A, 4B, 5A, 5B. As shown in FIGS. 7, 8, 9, and 10, each of the probe heads 34, 52, 66, 76 is provided on a proximal side with a respectively internally threaded recess 100, 102, 104, 106 for screwably coupling with an externally threaded tip portion 108, 110, 112, 114 of the respective distal shank section 32, 48, 64, 74. After insertion of distal tip portion 108, 110, 112, 114 into the internally threaded recess 100, 102, 104, 106 of the respective probe head 34, 52, 66, 76, the distal end is finished machined for shape and frequency. Again, for more security, the head 34, 52, 66, 76 may be beam welded, brazed or glued in place. Probes utilizing both these techniques have successfully been used and sterilized in dozens of procedures without failure.

Figure 11:
FIG. 11 is an exploded partial longitudinal cross-sectional view depicting an assemblable ultrasonic lipectomy probe in accordance with the present invention.

In cases where the overall length of the probes must be longer than can be successfully gun drilled, even with the opposing end procedure, the probes may be designed to be assembled from different sections threaded together in the operating theater. Accordingly, as illustrated in FIG. 11, an ultrasonic lipectomy probe 116 similar to the probe of FIG. 1 comprises an elongate shank or shaft 118 including a proximal shank section 120, a central shank section 122, and a distal shank section 124 distinguished from one another by decreasing external diameters. Shank 118 is formed from two shank pieces 126 and 128 joined to one another at an antinode 130, or place of maximum vibratory amplitude, since this generally coincides with the place of lowest internal stress. This facilitates manufacture of the ultrasonic lipectomy probe and further facilitates repair or replacement of the distal end of the probe. This manufacturing or assembly method may be used in any of the ultrasonic lipectomy probes described herein.

Shank piece 126 is provided at one end with an internally threaded recess 132 which receives an externally threaded projection 134 at one end of shank piece 128. The threads allow the probe to be assembled with standard wrenches in the field. The configuration of FIG. 11 has the slight advantage that distal shank piece 128 of probe 116, which is the area of greatest wear due to cavitational erosion, may be replaced while proximal shank piece 126 can be reused indefinitely. A slightly lower cost of replacement is then afforded the customer. It also allows the use of aluminum alloy for proximal piece 126 of larger probes, which eases drilling and machining, as well as lowers the material costs. However, this must be balanced against the cost of machining the threads in both shank pieces 126 and 128, as well as the possibility of failure due to heating at the interface of probe pieces 126 and 128.

A further improvement to the design of the ultrasonic liposuction probes comes as a consequence of the gun drilling process. By drilling the proximal end of an ultrasonic lipectomy probe with a slightly larger diameter hole than the distal half, the bore or suction channel is effectively increased in diameter from the distal end to the proximal end. Therefore, any material entering the probe at the distal end has less of a chance of jamming or clogging the probe, since the diameter is increasing as the material is conveyed to a suction bottle. This can be enhanced by designing the transducer to have a larger inner diameter than the cannula. In this way, clogging has been eliminated as a problem in equipment used in clinical trials. Where the probe diameter is small, on the order of 2 to 4 mm, or where the quantity of probes needed would make extruding custom tubing cost effective, the probes may be machined from thick wall tubing, instead of billet. Then the gun drilling step is not needed. All of the principles of design and manufacture apply to this case as well. It should be noted that the concept of shaping the probes' external dimensions to provide staged gain and lower stress in the shank and distal portions of the probe can be done even when the probe is solid and has no central bore. This is important in cases where the outer diameters of the probes must be fairly small, on the order of 1 to 3 mm. Some facial applications require these dimensions and preclude aspirating the liquefied tissue through the probe. In most cases, the liquefied tissue may be left in place, wherein the body will absorb the material naturally without harm to the patient. In other cases, the probe may be withdrawn and a standard aspirating needle inserted for removal of the tissue.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. An ultrasonic lipectomy probe device comprising:

a shank having a proximal end and a distal end;

means at said proximal end of said shank for connecting said shank to a source of ultrasonic vibrational energy; and an enlarged head at said distal end of said shank;

wherein said shank is provided with a longitudinally extending channel, said head being provided with at least one inlet bore communicating with said channel and extending at a substantial angle to said channel.

2. The device defined in claim 1 wherein said head includes a recess, said distal end of said shank being inserted in said recess.

3. The device defined in claim 2 wherein said shank is provided with a longitudinally extending channel, said head being provided with a pair of inlet bores communicating with said channel and extending at substantial angles to said channel on substantially opposite sides thereof.

4. The device defined in claim 1 wherein said shank includes at least one section of reduced external diameter at said distal end for amplifying an amplitude of vibration at said head relative to a magnitude of vibration at said proximal end of said shank.

5. The device defined in claim 1 wherein said longitudinally extending channel has a diameter which is greater at said proximal end of said shank than at said distal end of said shank.

6. The device defined in claim 1 wherein said shank includes a proximal section of a first external diameter, a central section of a second external diameter and a distal section of a third external diameter, said first external diameter being greater than said second external diameter, said second external diameter being greater than said third external diameter, whereby power output of the device is increased.

7. An ultrasonic lipectomy probe device comprising:

a shank having a proximal end and a distal end;

means at said proximal end of said shank for connecting said shank to a source of ultrasonic vibrational energy; and an enlarged head at said distal end of said shank, wherein said head includes a plug element inserted into a recess in said distal end of said shank.

8. An ultrasonic lipectomy probe device comprising:

a shank having a proximal end and a distal end;

means at said proximal end of said shank for connecting said shank to a source of ultrasonic vibrational energy; and an enlarged head at said distal end of said shank, wherein said head has a width, in a first direction, substantially larger than an outer diameter of said shank at said distal end thereof, said head having a thickness, in a second direction essentially orthogonal with respect to said first direction, substantially equal to said outer diameter of said shank.

9. The device defined in claim 8 wherein said shank is provided with a longitudinally extending channel, said head being provided with a pair of inlet bores communicating with said channel and extending at substantial angles to said channel.

10. The device defined in claim 9 wherein said inlet bores extend at substantial angles to said channel on substantially opposite sides thereof.

11. The device defined in claim 8 wherein said first direction and said second direction are both substantially orthogonal to said channel.

12. The device defined in claim 8 wherein said head includes a recess receiving said distal end of said shank.

13. The device defined in claim 8 wherein said shank includes a plurality of distinct shank pieces joined to one another at an antinode.

14. An ultrasonic lipectomy probe device comprising:

a shank having a proximal end and a distal end;

means at said proximal end of said shank for connecting said shank to a source of ultrasonic vibrational energy; and an enlarged head at said distal end of said shank, said shank including a plurality of distinct shank pieces joined to one another at an antinode, said shank being provided with a longitudinally extending bore having a plurality of diameters decreasing from said proximal end towards said distal end.

15. A method for manufacturing an ultrasonic lipectomy probe, comprising the steps of:

providing an elongate shank section;

forming a longitudinally extending channel in said shank section;

providing a plug element with at least one inlet bore; and inserting said plug element into said channel at a distal end of said shank section so that said bore communicates with said channel and so that said bore extends at a substantial angle to said channel.

16. The method defined in claim 15, further comprising the step of bonding said plug element to said shank section upon completion of said step of inserting.

17. The method defined in claim 16 wherein said step of bonding includes at least one of the following steps:

beam welding said plug element to said shank section;

brazing said plug element to said shank section; and gluing said plug element to said shank section.

18. The method defined in claim 15 wherein said plug element is provided with an external screw thread, further comprising the step of forming an internal screw thread at said distal end of said channel, said step of inserting including the step of screwing said plug element into said channel.

19. A method for manufacturing an ultrasonic lipectomy probe, comprising the steps of:

providing an elongate first shank section and an elongate second shank section; and connecting said first shank section to said second shank section at a junction point to form a completed probe shank, said first shank section and said second shank section having predetermined lengths so that said junction point is located at an antinode of said probe shank.

20. The method defined in claim 19 wherein said step of connecting includes the step of bonding one end of said first shank section to a preselected end of said second shank section.

21. The method defined in claim 20 wherein said step of bonding includes at least one of the following steps:

beam welding said one end of said first shank section to said preselected end of said second shank section;

brazing said one end of said first shank section to said preselected end of said second shank section; and gluing said one end of said first shank section to said preselected end of said second shank section.

22. The method defined in claim 19, further comprising the steps of:

providing said first shank section with means at one end of said first shank section for connecting said first shank section to a source of ultrasonic vibrational energy; and forming longitudinally extending channels in said first shank section and said second shank section, said step of connecting including the step of connecting another end of said first shank section to a first end of said second shank section at said junction point so that the channels in said first shank section and said second shank section communicate with one another in the completed ultrasonic probe shank.

23. The method defined in claim 22 wherein one of said another end and said first end is provided with an external screw thread and the other of said another end and said first end is provided with an internal screw thread, further comprising the step of screwing said first shank section and said second shank section to one another.

24. The method defined in claim 19, further comprising the steps of:

forming an incision in a skin surface of a patient;

upon connection of said first shank section to said second shank section, inserting a distal end segment of said probe shank through said incision and into subcutaneous adipose tissues of the patient;

upon insertion of said distal end segment through said incision, generating an ultrasonic pressure wave at a proximal end of said probe shank;

transmitting said ultrasonic wave through said probe shank to establish a longitudinal standing wave therein;

producing cavitation bubbles at a distal tip of said probe shank in response to said standing wave; and by virtue of the production of said cavitation bubbles, liquefying adipose tissues of the patient at a surgical site located distally of said distal tip.

25. An ultrasonic lipectomy method comprising the steps of:

providing an ultrasonic lipectomy probe device comprising a shank having a proximal end and a distal end, means at said proximal end of said shank for connecting said shank to a source of ultrasonic vibrational energy, and an enlarged head at said distal end of said shank;

forming an incision in a skin surface of a patient;

inserting said head and a distal end segment of said shank through said incision and into subcutaneous adipose tissues of the patient;

upon insertion of said head through said incision, generating an ultrasonic pressure wave at said proximal end of said shank;

transmitting said ultrasonic wave through said shank to establish a longitudinal standing wave therein;

producing cavitation bubbles at said head in response to said standing wave;

by virtue of the production of said cavitation bubbles, liquefying adipose tissues of the patient at a surgical site located distally of said head; and during said steps of generating, transmitting, producing and liquefying, manipulating said probe device from outside the patient so that said head moves from side to side.

26. The method defined in claim 25 wherein said shank has a channel extending longitudinally from said proximal end to said distal end, further comprising the step of applying suction to said channel during said step of manipulating, thereby aspirating the liquefied adipose tissues from said surgical site through said channel.

27. The method defined in claim 26 wherein said head is provided with a pair of inlet bores communicating with said channel and extending at substantial angles to said channel, further including the step of aspirating the liquefied adipose tissues from said surgical site through said inlet bores and into said channel.

* * * * *